United States Patent [19]

Kane

[11] 3,997,606
[45] Dec. 14, 1976

[54] METHOD OF PRODUCING DRY ACRYLAMIDE

[75] Inventor: James Kane, Olympia Fields, Ill.

[73] Assignee: Nalco Chemical Company, Oak Brook, Ill.

[22] Filed: Dec. 3, 1975

[21] Appl. No.: 637,252

[52] U.S. Cl. .................................. 260/561 N
[51] Int. Cl.² ............................... C07C 103/133
[58] Field of Search ........................ 260/561 N

[56] References Cited

UNITED STATES PATENTS

| | | |
|---|---|---|
| 3,274,245 | 9/1966 | Bobsein et al. .......... 260/561 N |
| 3,624,154 | 11/1971 | Robbins et al. .......... 260/561 N |
| 3,666,809 | 5/1972 | Okuno et al. ........... 260/561 N |
| 3,674,848 | 7/1972 | Schoenbrunn ........ 260/561 N X |
| 3,686,307 | 8/1972 | Greene et al. .......... 260/561 N |
| 3,917,693 | 11/1975 | Asano et al. ........... 260/561 N |
| 3,920,740 | 11/1975 | Svarz et al. ............ 260/561 N |
| 3,923,741 | 12/1975 | Asano et al. ........... 260/561 N |
| 3,941,837 | 3/1976 | Asano et al. ........... 260/561 N |
| 3,956,387 | 5/1976 | Dockner et al. ........ 260/561 N |

*Primary Examiner*—Daniel E. Wyman
*Assistant Examiner*—Thomas A. Waltz
*Attorney, Agent, or Firm*—John G. Premo; Robert A. Miller; Barry W. Sufrin

[57] ABSTRACT

Dry acrylamide is produced by reacting acrylonitrile with from 0.3 to 1 mole of water in the presence of a metallic nitrile conversion catalyst. The reaction is conducted under conditions of pressure and temperature and other reaction conditions to convert at least 30% by weight of the nitrile to acrylamide. This reaction produces a solution of acrylamide dissolved in nitrile which then is either treated by means of cooling or pressure reduction to precipitate acrylamide crystals from the reaction mixture, which crystals are then recovered.

2 Claims, 1 Drawing Figure

% ACRYLAMIDE YIELD VS. $H_2O$/ACN FEED RATIO

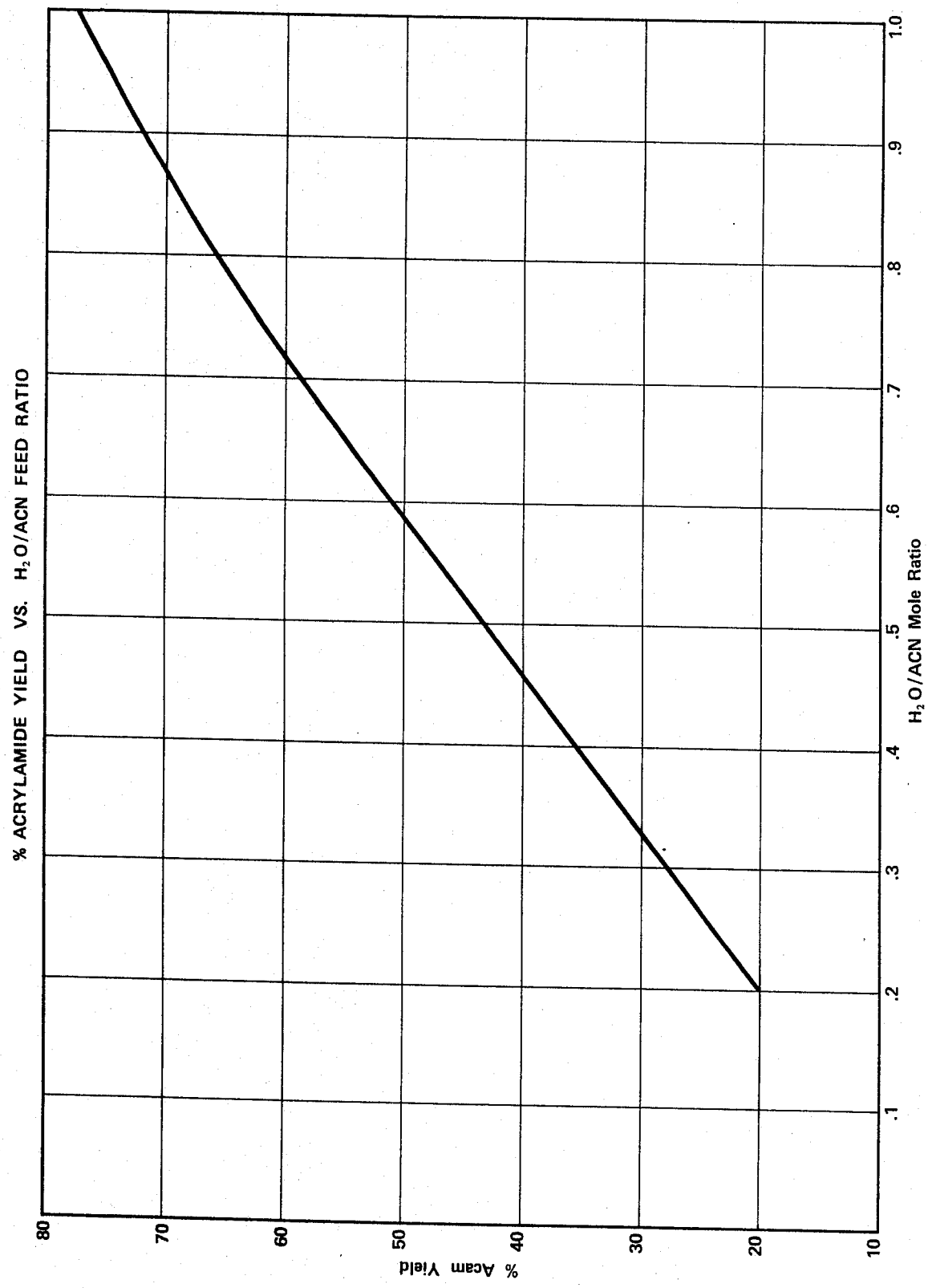

METHOD OF PRODUCING DRY ACRYLAMIDE

INTRODUCTION

It is now known that acrylamide can be produced by reacting acrylonitrile with water in the presence of a metallic conversion catalyst. These catalytic processes are now being used on a commercial scale. It is common in these processes to react about 7% acrylonitrile dissolved in water in the presence of these metallic catalysts whereby a dilute aqueous solution of acrylamide is produced. In order to produce dry acrylamide by these catalytic conversion processes, it is necessary to remove large quantities of water using evaporative techniques. The energy required to evaporate such large quantities of water adds greatly to the cost of producing dry acrylamide by catalytic processes. If it were possible to directly produce dry acrylamide from catalytic processes of the type described above, an improvement in the manufacture of dry acrylamide would be afforded.

THE INVENTION

In accordance with my invention, it has been discovered that dry acrylamide is readily produced by reacting acrylonitrile with from 0.3 to 1 mole of water in the presence of a metallic nitrile conversion catalyst under conditions including the use of elevated temperature and pressure whereby at least 30% by weight of the nitrile is converted to acrylamide. The acrylamide at this point in my process is in the form of a solution within the nitrile-water mixture. Upon release of the pressure which includes the use of vacuum and/or with cooling, the acrylamide crystallizes from the reaction mixture and may be readily removed therefrom. These crystals are characterized as containing 0.5% by weight or less of acrylonitrile and less than 5% by weight of water.

The Metallic Nitrile Conversion Catalyst

During the last several years, numerous metallic catalysts for converting nitrile and water into amides have been patented or described in the literature. A summary of these catalysts as well as literature references thereto is set forth below:

| Catalyst | Literature Reference |
| --- | --- |
| Raney copper, Ullman copper, reduced copper, copper on a carrier, silver cobalt, nickel, palladium and platinum. | Canadian Patent 899,380 |
| Copper in combination with nickel, chromium manganese, zinc, molybdenum, as well as oxides or sulfides of said metal. | Canadian Patent 930,377 |
| Combinations consisting essentially of 10 to 90% by weight of oxides of copper, silver, zinc or cadmium and 10 to 90% by weight of oxides of chromium or molybdenum. | U.S. 3,597,481 |
| Urushibara - copper chloride precipitate with zinc dust. | Watanabe in Bull, Chem., Soc. Japan, 37,1325 (1964) |
| Copper, copper oxide, copper-chromium oxide, copper-molybdenum oxide or mixtures thereof. | U.S. 3,631,104 |
| Reduced copper oxides in combination with other metal oxides, particularly rare earth metal oxides. | U.S. 3,696,152 |
| Copper prepared by reducing copper hydroxide or a copper salt. | U.S. 3,758,578 |
| Copper metal. | U.S. 3,767,706 |
| Highly active Raney copper. | U.S. 3,920,740 |
| Zinc and cadmium oxides. | German 551,869 |
| Lithium hydroxide. | U.S. 3,686,307 |
| Ruthenium, rhodium, palladium, osmium, iridium or platinum. | U.S. 3,670,021 |
| Fatty acid salts of cadmium, zinc, copper, cobalt, lead, tin, titanium, nickel, iron, mercury; sulfates, nitrates and halides of lead, tin, titanium, nickel, iron, mercury; tin, cadmium and copper oxides; copper powders. | Jap. 70/21, 295, Inoue et al., Ashi Kasei Co., 7-18-70. |
| Cupric hydroxide, manganese dioxide, chromium, tungsten, iron or nickel oxide. | Japan 72/33,327 |
| Boron hydroxide and inorganic phosphorous containing acids. | Japan 73/36118 |
| Cobalt chromium catalyst. | Japan 73/39424 |
| Nickel chromium catalyst. | Japan 73/39426 |
| Ruthenium or rhodium. | Japan 73/54,021 |
| Manganese dioxide. | Haefele et al., Ind. Eng. Chem. Prod. Res. Develop. 11(3), 364–365 (1972) |
| Zinc, copper, cobalt and cadmium thiocyanates, sulfates, nitrates, halides and cyanides as well as metallic zinc and metallic copper. | Spanish Patent Application Public No. 695205 |
| Metal salts of cation exchange resins. | U.S. 3,674,848 |
| Cuprous dihydrogen phosphate. | U.S. 3,679,745 |
| Copper salts or copper salts | U.S. 3,381,034 |

| Catalyst | Literature Reference |
|---|---|
| plus copper metal. | |

Of the above catalysts, I prefer to use in the practice of my invention a special Raney copper catalyst which contains from about 2 to 45% by weight of aluminum. This catalyst in its preferred embodiment contains particles having an average particle diameter ranging from 0.002 to 0.5 inches and has a relative activity of at least about 2. Catalysts of this type as well as their method of preparation are disclosed in U.S. Pat. No. 3,920,740, the disclosure of which is incorporated herein by reference.

As will be shown hereafter, it is important that the metallic catalyst be capable of producing acrylamide from acrylonitrile and water in yields of at least 30% and, preferably, at least 50%. In certain instances, certain of the catalysts listed above are incapable of producing acrylamide in such yields under normal commercial operating conditions. It is understood, therefore, that only those catalysts capable of producing acrylamide in a 30% yield are intended to be included in my definition of a metallic conversion catalyst.

The Reaction Conditions

The most important parameter of my invention resides in using from between .3 to 1 mole of water per mole of nitrile during the conversion of the nitrile to the acrylamide. More preferably, I prefer to use between 0.35 to 1 mole of water per mole of acrylonitrile.

Many of the references cited above state in very general terms that small amounts of water in relation to nitrile may be used to produce amides from nitriles. For instance, in U.S. Pat. No. 3,674,848 it is suggested that the catalytic conversion of acrylonitrile to acrylamide may use between 0.05 to 20 moles of water per mole of acrylonitrile. A careful study of this reference, however, indicates that it is preferred to use in excess of 1 mole of water for the best results to be achieved. Similarly, in U.S. Pat. No. 3,631,104, 1 mole or more of water is suggested but, again, the preferred embodiment indicates that molar excesses of water are preferred.

When small quantities of water are used in relation to nitrile, many of the references cited above show that the conversion of nitrile to acrylamide is of a very low order of magnitude. It is believed that none of the references disclose using between .3 - 1 mole of water in the presence of a metallic conversion catalyst to produce the acrylamides in yields greater than 30%.

It is to be understood, however, that many of the catalysts may be capable of producing a 30% yield by adjusting the conditions of the reaction. This includes adjusting such conditions as the reaction temperature, the reaction time, the pressure and the like to produce acrylamide from acrylonitrile in yields of 30% or more. As previously indicated, in order to achieve such yields, many of the reactions would be impractical from a commercial standpoint. Thus, in certain instances, if extremely large excesses of the catalysts are used, high yields can be obtained, but the cost of the catalyst would be prohibitive commercially. It is for these reasons that I prefer to use in my process when it is practiced commercially only highly active catalytic species such as, for instance, those disclosed in U.S. Pat. No. 3,920,740.

With respect to the various temperatures and pressures that may be used as well as the quantity of catalyst, flow rates and the like, reference may be had to U.S. Pat. No. 3,920,740 as well as the teachings of U.S. Pat. No. 3,767,706. As indicated in this latter reference, the temperatures may range in a preferred mode of operation between 25° – 200° C.

The pressure may be as low as 15 lbs./sq. in. up to as high as 200 lbs./sq. in. If the catalyst is a solid and used in a fixed bed operational scheme, the flow rate can vary widely depending on the activity of the catalyst, the temperature and the pressure. A routine experimentation can determine optimum flow rates based on the other parameters discussed, particularly in view of the teachings of U.S. Pat. No. 3,920,740.

As previously indicated, the most important reaction condition of the invention resides in using between 0.3 to 1 mole of water and, preferably, at least 0.35 moles of water per mole of nitrile reacted in the presence of the metallic catalyst. To demonstrate the importance of this, I am presenting below the following illustrative example:

EXAMPLE 1

Using tube reactor 30 inches in length × 1.5 inch width and filled with 900 grams of (80 Cu/20 Al) Raney Copper Catalyst prepared generally in accordance with the teaching of U.S. Pat. No. 3,920,740, a conversion study of acrylonitrile to acrylamide was initiated. The mole ratio of water/acrylonitrile reaction mixture was varied from 0.2 to 1.

The conditions under which the above conversion study was done were:
1. Reaction temperature range — 118° – 120° C.
2. Reaction pressure range — 90 - 95 PSI
3. Reagent flow rate — 550 cc/hr.

The result that conversion indicates is that the maximum conversion of acrylonitrile to acrylamide occurred when one mole of each reactant was fed (mole ratio = 1) as the feed stock.

The resultant acrylamide, acrylonitrile, water reaction mixture made from a 1:1 ratio of water-acrylonitrile was then spray dried, yielding a 95.4% dry acrylamide crystal containing 4.3% water and 0.3% acrylonitrile.

The results of these experiments are plotted in the drawing.

With specific reference to the drawing, it should be noted that when more than .6 moles and up to 1 mole of water are used, that the conversion is increased. It is, of course, obvious that water would not be used in excess of 1 mole since this would leave excessive water in the reaction which would dissolve acrylamide, thereby making water evaporation necessary.

One of the surprising discoveries upon which this invention is predicated is that when at least 30% and, preferably, at least 50% of the nitrile is converted to acrylamide under conditions of temperature and pressure that when such reaction mixture is either cooled the pressure released, which includes placing the reaction media under a vacuum, that the acrylamide suspended in the reaction media crystallizes and upon recovery is relatively free of entrained nitrile or water.

The crystallization of acrylamide under optimum conditions can, at times, be almost termed as dramatic. Using the reaction conditions previously specified and conducting the reaction to produce a conversion of 70% of nitrile into acrylamide and then subjecting the reaction media to a vacuum of 18 psi, crystallization is almost instantaneous and resembles a blizzard in the flash tank.

When the conversion of acrylonitrile to acrylamide is less than 50%, it is necessary to use either high vacuum conditions either alone or with cooling Eg 0° C. or lower to produce crystallization of the acrylamide.

It is apparent that my process may be conducted either as a batch or as a continuous process. Unreacted nitrile and water can be vacuum or flash evaporated with the nitrile being returned for recycle or recovery. The water is preferably discarded since it tends to be contaminated with organic impurities.

Using my process, it is possible to readily produce dry acrylamide which has many industrial uses, the most common of which is the preparation of acrylamide polymers. Much of the commercial acrylamide today is produced as a 50% aqueous solution. If such solutions are shipped, freight must be paid for the shipment of the water. With my process, it is possible to produce substantially dry acrylamide which can be shipped in large quantities at a substantial savings.

Having thus described my invention, it is claimed as follows:

1. A method of producing acrylamide containing less than 5% water which comprises reacting acrylonitrile with from 0.3 to 1 mole of water in the presence of a metallic nitrile conversion catalyst under reaction conditions whereby at least 30% by weight of the nitrile is converted to acrylamide which is dissolved within the nitrile water mixture and then directly reducing the pressure or temperature or both pressure and temperature of said mixture whereby acrylamide crystals are formed and then recovering said crystals.

2. The method of claim 1 where at least 50% of the nitrile is converted to acrylamide, the amount of water to acrylonitrile ratio is within the range of 0.6 to 1 mole and the metallic nitrile conversion catalyst is a Raney copper catalyst which contains from about 2 to 45% by weight of aluminum.

* * * * *